US00PP24591P2

(12) United States Plant Patent
Eggleton

(10) Patent No.: US PP24,591 P2
(45) Date of Patent: Jul. 1, 2014

(54) ***VIOLA* PLANT NAMED 'SMEV4'**

(50) Latin Name: *Viola hybrida*
Varietal Denomination: SMEV4

(71) Applicant: Steve Eggleton, Wonga Park (AU)

(72) Inventor: Steve Eggleton, Wonga Park (AU)

( * ) Notice: Subject to any disclaimer, the term of this patent is extended or adjusted under 35 U.S.C. 154(b) by 0 days.

(21) Appl. No.: 13/986,005

(22) Filed: Mar. 22, 2013

(51) Int. Cl.
*A01H 5/00* (2006.01)

(52) U.S. Cl.
USPC ..... Plt./323

(58) Field of Classification Search
USPC ..... Plt./323
See application file for complete search history.

(56) References Cited

U.S. PATENT DOCUMENTS

PP23,033 P2 * 9/2012 Eggleton ..... Plt./323

* cited by examiner

*Primary Examiner* — June Hwu
*Assistant Examiner* — Keith Robinson
(74) *Attorney, Agent, or Firm* — Cassandra Bright

(57) ABSTRACT

A new cultivar of *Viola* plant named 'SMEV4' that is distinguishable by compact dome-shaped habit, fragrant tri-colored flowers consisting of dark violet upper petals, mid-violet lateral petals and a golden yellow lower petal. The lateral and lower petals exhibit prominent dark violet veins. 'SMEV4' is hardy in USDA Zone 5 and blooms from early spring through fall.

2 Drawing Sheets

Latin name of the genus and species: *Viola hybrida*.
Denomination: 'SMEV4'.

BACKGROUND OF THE INVENTION

The present invention relates to a new and distinct cultivar of *Viola* known commonly as violet and grown for use in border, container, and landscape. The new invention from the family Violaceae is known botanically as *Viola hybrida* and will be referred to hereinafter by the cultivar name 'SMEV4'.

'SMEV4' resulted from a formal breeding program developed by the inventor, and conducted in Wonga Park, Victoria, Australia with the goal of producing a series of perennial *Viola* exhibiting a range of flower colors borne on plants with a uniform dense domed habit. The breeding program commenced in 2001.

'SMEV4' is a hybrid seedling selection that resulted from the controlled cross-pollination in December 2006 of the female parent, *Viola* 'Tiger Eyes' (non-patented) and the male parent, *Viola* 'Lord Primrose' (U.S. Plant Pat. No. 18,253). The resulting seed was collected, sown and raised to flowering during 2007. From an approximate 150 seedlings, ten were selected by the inventor, and then propagated asexually by cuttings. From these ten, 'SMEV4' was selected in March 2008 based on the criteria of novel flower color and prolific flower number.

'SMEV4' is distinguishable from each of its parents by flower color as follows. The flowers of 'SMEV4' are tri-colored, consisting of dark violet upper petals, mid-violet lateral petals and a golden yellow lower petal. In addition, the lateral and lower petals of 'SMEV4' exhibit dark violet veins. The flowers of the female parent are golden yellow throughout except for dark brown to black central blotch and radiating veins. The flowers of the male parent are bi-colored, predominantly mauve with small yellow centers and absence of dark blotch or veins.

The closest comparison plant in commerce known to the inventor is the male parent, *Viola* 'Lord Primrose', with which 'SMEV4' is compared above.

The first asexual reproduction of 'SMEV4' was accomplished in 2008 in a cultivated area of Victoria, Australia. Asexual propagation was accomplished by the inventor, using the method, of vegetative cuttings. Since that time 'SMEV4' has been determined stable and true to type in subsequent generations of asexual propagation.

SUMMARY OF THE INVENTION

The following traits have been repeatedly observed and represent the distinguishing characteristics of the new *Viola* cultivar named 'SMEV4'. These traits in combination distinguish 'SMEV4' from all other existing varieties of *Viola* known to the inventor. 'SMEV4' has not been tested under all possible conditions and phenotypic differences may be observed with variations in environmental, climatic, and cultural conditions, however, without any variance in genotype.

1. 'SMEV4' exhibits compact dome-shaped habit.
2. 'SMEV4' exhibits green glossy foliage.
3. 'SMEV4' produces numerous flowers on short peduncles.
4. The flowers of 'SMEV4' are tri-colored, consisting of dark violet upper petals, mid-violet lateral petals and a golden yellow lower petal.
5. The lateral and lower petals of 'SMEV4' exhibit prominent dark violet veins.
6. The flowers of 'SMEV4' are pleasantly fragrant with the characteristic perfume of violets.
7. After one year of growth from a rooted cutting 'SMEV4' is 20 cm. in height including the flowers, and 20 cm. in width.
8. 'SMEV4' is hardy to USDA Zone 5.
9. 'SMEV4' blooms from early spring through fall.

BRIEF DESCRIPTION OF THE DRAWINGS

The accompanying color drawings illustrate the overall appearance of the new *Viola* cultivar named 'SMEV4' showing color as true as is reasonably possible to obtain in color reproductions of this type. Color in the drawings may differ from the color values cited in the detailed botanical description, which accurately describe the actual color of the new variety 'SMEV4'. Both drawings were made from a plant which has been grown in an unheated greenhouse in Arroyo Grande, Calif. No pinching or chemical growth regulators have been employed. Both drawings were made using conventional techniques and although flower and foliage color may appear different from actual color due to light reflectance, they are as accurate as possible by conventional photography. Below is s a description of each of the figures.

BOTANICAL DESCRIPTION OF THE PLANT

Figure 1:
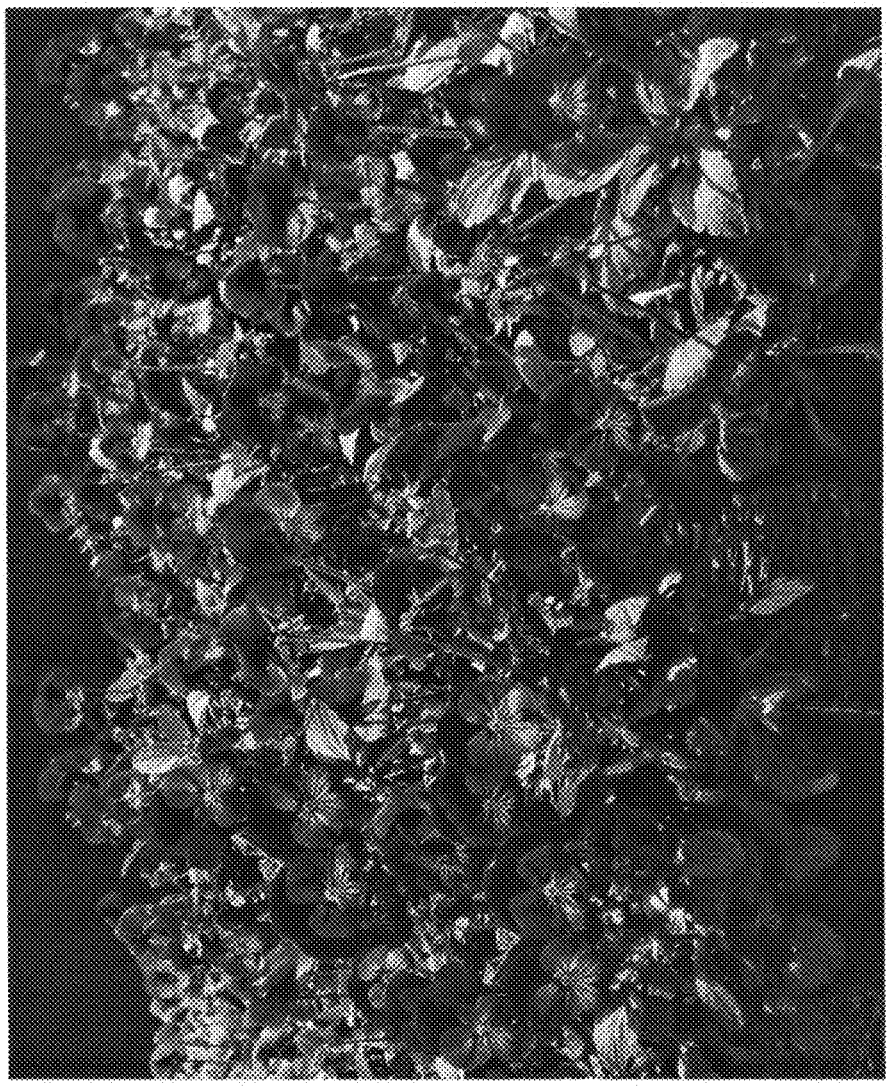
FIG. 1 depicts a 6 months old plant in its first season of bloom in a 12 cm diameter container.
Figure 2:
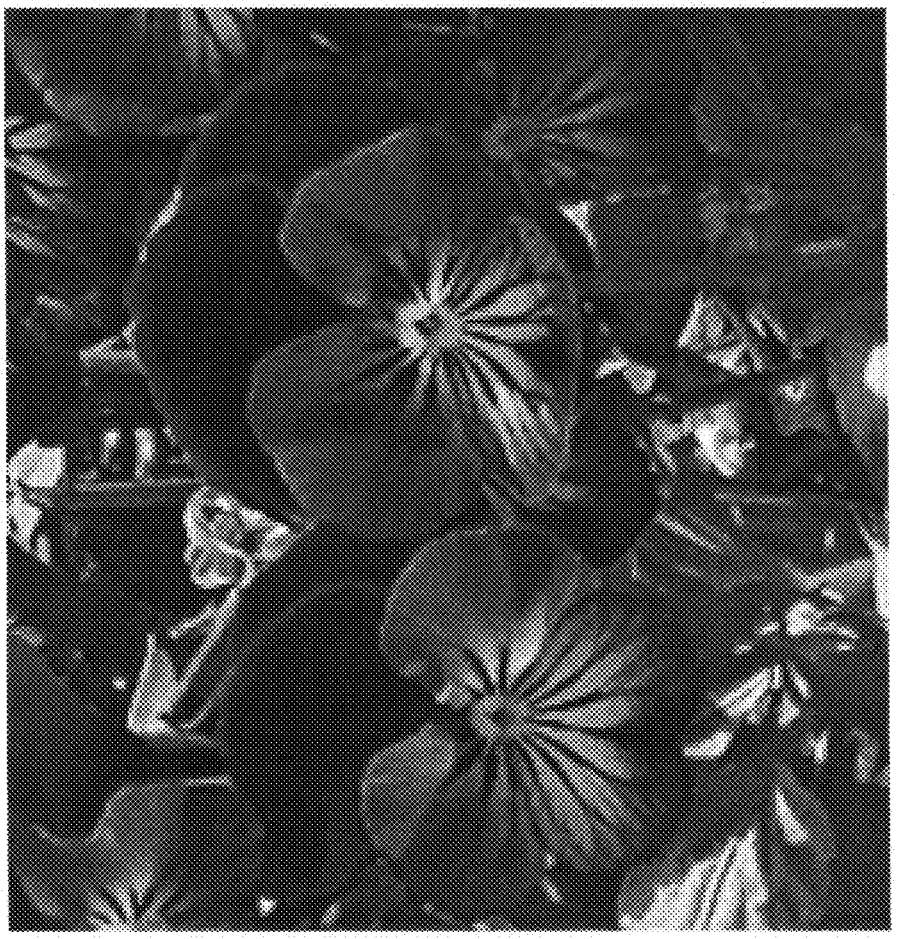
FIG. 2 depicts a close-up view of a flower on the plant shown in FIG. 1.

The following is a detailed botanical description of the new *Viola* cultivar named 'SMEV4'. Observations and measurements were collected from a six months old plant which has been grown in an unheated greenhouse in Arroyo Grande, Calif. Color determinations were made in accordance with the 2007 edition of The Royal Horticultural Society Colour Chart from London, England, except where general color terms of ordinary dictionary significance are used.

Botanical classification: *Viola hybrida* 'SMEV4'.

PROPAGATION

Propagation method: Vegetative cuttings.
Rooting system: Fine and fibrous.
Time to develop roots (range): 14-20 days to develop roots on an initial cutting.
Temperature to develop roots: The recommended air temperature is 20-21° Centigrade.

PLANT

Habit: Compact.
Shape: Dome-shaped.
Type: Perennial.
Vigor: Moderate.
Crop time (range): Under summer growing conditions, 'SMEV4' will flower and be saleable in a 10 cm container in flower after 3 months of growing from an unrooted cutting. During winter and spring months in an unheated greenhouse 'SMEV4' flowers and is saleable in 4-6 months depending on light levels and day length.
Plant dimensions: 20 cm. in height including the flowers, and 20 cm. in width.
Cultural requirements: Consistently moist soil or container medium.
Stem:
*Branching*.—Basal.
*Stem color*.—N144C.
*Stem length* (*average*).—5 cm.
*Stem width*.—0.25 cm.
*Stem shape*.—Cylindrical.
*Stem surface*.—Glabrous.
*Internode* (*average*).—0.75 cm.

FOLIAGE

Type: Evergreen.
Leaf arrangement: Alternate.
Leaf division: Simple.
Leaf quantity (average): 6.
Margin: Crenate.
Leaf shape: Ovate.
Leaf length (range): 2.0 cm-3.50 cm.
Leaf width (range): 1.50 cm-2.25 cm.
Leaf color (abaxial surface): 137C.
Leaf color (adaxial surface): 137A.
Leaf base: Rounded.
Leaf apex: Rounded.
Venation: Pinnate.
Vein color (abaxial and adaxial surfaces): 137C.
Leaf surface (abaxial and adaxial): Glabrous.
Leaf attachment: Petiolate.
Petiole color: 138B.
Petiole dimensions (average): 2 cm. in length and 1 mm. in width.
Petiole shape: Sulcate.
Petiole surface: Glabrous.
Stipules: Present and persistent.
Stipule form: Leaf-like.
Stipule margin: Cleft.
Stipule apex: Rounded.
Stipule base: Truncate.
Stipule color: 138B.
Stipule surface (abaxial and adaxial): Glabrous.
Stipule attachment: Sessile.
Stipule dimensions (average): 1.50 cm. in length and 0.50 cm. in width.

FLOWER

Inflorescence: Solitary flower consisting of five petals.
Inflorescence quantity: Approximately 10 open and opening flowers, per branch.
Aspect (range): Facing outward to pendant.
Inflorescence width: 3.5 cm.
Inflorescence length: 4.0 cm.
Inflorescence depth: 2.0 cm.
Inflorescence arrangement: Terminal inflorescence.
Inflorescence shape: Rotate.
Fragrance: Moderate to strong typical *Viola* fragrance.
Inflorescence self-cleaning or persistent: Self-cleaning.
Inflorescence fragrance: Pleasant scent characteristic of violets.
Lastingness of inflorescence (range): 5-7 days.
Blooming seasons: Early spring through fall.
Peduncle length (range): 5.50 cm-7 cm.
Peduncle width: 3 mm.
Peduncle shape: Sub-cylindrical.
Peduncle surface: Glabrous.
Peduncle color: 144B.
Peduncle strength: Flexible.
Bud color: 143B.
Bud shape: Elongated oval.
Bud dimensions (average): 1.30 cm. in length and 0.40 cm in width.
Bud surface: Glabrous.
Bud apex: Rounded.
Corolla tube depth: 6 mm.

Petal quantity: 5, consisting of 2 upper petals, 2 lateral petals, and 1 lower petal.
Spur: 1 present on lower petal.
Spur color: 144B.
Spur dimensions: 3 mm. in length and 1.50 mm. in width.
Upper petals (two):
*Petal shape*.—Reniform.
*Petals fused or unfused*.—Unfused.
*Petal apex*.—Rounded.
*Petal base*.—Truncate to cuneate.
*Petal margin*.—Entire, lightly undulating.
*Petal length*.—1.7 cm-2.0 cm.
*Petal width*.—2.2 cm-2.5 cm.
*Petal color* (*both surfaces*).—N92B.
*Petal surface* (*both surfaces*).—Glabrous.
Lateral petals (two):
*Petal shape*.—Reniform.
*Petals fused or unfused*.—Fused.
*Petal apex*.—Rounded.
*Petal base*.—Truncate.
*Petal margin*.—Entire, lightly undulating.
*Petal length*.—1.2 cm-1.5 cm.
*Petal width*.—1.5 cm-1.8 cm.
*Petal color* (*both surfaces*).—86A, becoming lighter towards base, N87D at base. Veins N186B.
*Petal veins*.—Approximately 5 in number, radiating from petal base, length between 0.2 cm and 0.5 cm, width 0.5 cm.
*Petal surface* (*both surfaces*).—Glabrous.
Lower petal (one):
*Petal shape*.—Obcordate.
*Petals fused or unfused*.—Fused.
*Petal apex*.—Emarginate.
*Petal base*.—Truncate.
*Petal margin*.—Entire, lightly undulating.
*Petal length*.—1.5 cm-1.7 cm.
*Petal width*.—2.0 cm-2.2 cm.
*Petal color* (*adaxial surfaces*).—Predominantly golden yellow 17A, becoming mauve 70A and violet 83A towards margin, dark violet N92B at emarginate apex and violet blue N92A veins.
*Petal veins*.—Approximately 10 in number, radiating from petal base, length between 0.5 cm and 1.0 cm, width 0.5 cm.
*Petal surface* (*both surfaces*).—Glabrous.

Calyx shape: Stellate.
Calyx diameter: 2 cm.
Sepals: 5 in number.
Sepal dimensions: 1 cm. in length and 0.40 cm. in width.
Fused or unfused: Sepals unfused.
Sepal color (both surfaces): 138A.
Sepal apex: Acute.
Sepal base: Truncate.
Sepal surface: Glabrous.
Sepal margin: Entire. Sepal shape: Lanceolate.

REPRODUCTIVE ORGANS

Stamen quantity: 5 joined around ovary.
Stamen length: 4 mm.
Stamen color: 145D.
Anther length: <1 mm. appendage to stamen.
Anther width: 2.50 mm.
Anther color: 164A.
Pollen color: 155C.
Pollen quantity (range): Moderate to heavy.
Pistil quantity: 1.
Pistil height: 6.5 mm.
Style height: 1 mm.
Style color: N144A.
Stigma dimensions: <1 mm. in height and 1 mm. in diameter.
Stigma color: N144A.
Stigma shape: Globular.
Stigma surface: Glandular.
Ovary position: Superior.
Ovary color: N144A.
Ovary shape: Dome-shaped.
Ovary dimensions: 6 mm. in height and 3 mm. in width.

OTHER CHARACTERISTICS

Seeds and fruits: Not observed to date.
Disease/pest resistance: Neither resistance nor susceptibility to the normal diseases and pests of *Viola* have been observed.
Hardiness: USDA Zone 5.

What is claimed is:

1. A new and distinct cultivar of *Viola* plant named 'SMEV4' as described and illustrated herein.

* * * * *